United States Patent [19]

Atkins

[11] 4,038,312

[45] July 26, 1977

[54] TRICYCLIC PHOSPHOROUS TRIAMIDES

[75] Inventor: Thomas Joseph Atkins, Wilmington, Del.

[73] Assignee: E. I. Du Pont de Nemours and Company, Wilmington, Del.

[21] Appl. No.: 730,519

[22] Filed: Oct. 7, 1976

Related U.S. Application Data

[63] Continuation-in-part of Ser. No. 606,778, Aug. 22, 1975, Pat. No. 3,996,276.

[51] Int. Cl.² ............................ C07F 9/02; C07F 9/65; C07F 9/22
[52] U.S. Cl. .................................. 260/551 P; 252/8.1
[58] Field of Search ..................................... 260/551 P

[56] References Cited

U.S. PATENT DOCUMENTS 3,987,128  10/1976  Richman ...................... 260/551 P X
3,996,276  12/1976  Atkins ............................. 260/551 P

OTHER PUBLICATIONS

Clardy et al., CA 81:112283y (1974).

Primary Examiner—Daniel E. Wyman
Assistant Examiner—Thomas A. Waltz

[57] ABSTRACT

Polycyclic phosphorous triamides of the formula

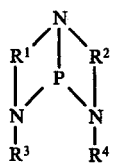

in which $R^1$ and $R^2$, alike or different, are alkylene of 2 to about 6 carbons;

$R^3$ and $R^4$, alike or different, are alkyl of 1 to about 8 carbons, cycloalkyl of 5 to about 8 carbons, or aralkyl where the aryl group is of 6 to about 12 carbons and the alkyl is of 1 to about 8 carbons; or $R^3$ and $R^4$ are joined together to form an alkylene group of 2 to about 6 carbons which may be interrupted by 1. a

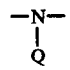

group where Q is hydrogen or alkyl of 1 to about 18 carbons, or 2. one or two —O— linkages;

there are at least 2 carbons between each two hetero atoms in the outer ring system, and when the triamide is tricyclic, at least one of the chains between the nitrogens linked to phosphorus contains at least three atoms are useful as flame retardants for cotton.

11 Claims, No Drawings

TRICYCLIC PHOSPHOROUS TRIAMIDES

CROSS-REFERENCE TO RELATED APPLICATION

This is a continuation-in-part of copending application Ser. No. 606,778 filed Aug. 22, 1975 now U.S. Pat. No. 3,996,276, and claims subject matter restricted from that application.

BACKGROUND OF THE INVENTION

1. Field of the Invention

This invention relates to polycyclic amides of phosphorous acid. More specifically, it relates to bicyclic and tricyclic triamides of phosphorous acid and their use as flame retardants for cotton.

2. Description of the Prior Art

Polycyclic phosphorous triamides and their carbon analogs are known, but no phosphorous triamides in which the amide nitrogens are annular hetero atoms in a single large ring are known. The closest prior art references are:

1. Stetter and Bremen, Chem, Ber., 106, 2523 (1973), disclose the following reaction:

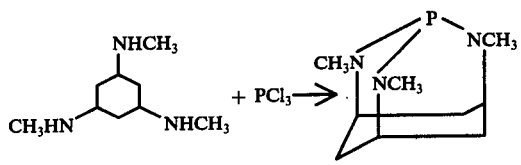

2. Laube et al., Inorg. Chem., 6, 173 (1967), disclose the transamidation reaction $P[N(CH_3)_2]_3$ +

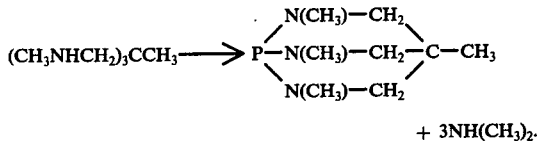

+ $3NH(CH_3)_2$.

3. Petrov et al., U.S.S.R. 144,172 (1962) (C.A., 57, 5583 (1962)), disclose transamidation of phosphorous amides by heating with amines of higher boiling point than those of the amines that composed the amide groups of the initial amides.

SUMMARY OF THE INVENTION

In accordance with this invention, polycyclic phosphorous triamides have been discovered which are of the formula:

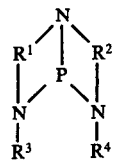

in which $R^1$ and $R^2$, alike or different are alkylene of 2 to about 6 carbons containing at least 2 carbons in the backbone, and $R^3$ and $R^4$, alike or different, are alkyl of 1 to about 8 carbons, cycloalkyl of 5 to about 8 carbons, or aralkyl where the aryl group is of 6 to about 12 carbons and the alkyl is of 1 to about 8 carbons, or $R^3$ and $R^4$ are joined together to form a divalent group selected from the group consisting of alkylene of 2 to about 6 carbons containing at least 2 carbons in the backbone,

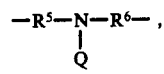

—$R^5$—O—$R^6$—, and
—$R^5$—O—$R^6$—O—$R^7$— where
$R^5$, $R^6$ and $R^7$, alike or different, are alkylene of 2 to about 6 carbons containing 2 to 3 carbons in the backbone, and Q is hydrogen or alkyl of 1 to about 18 carbons.
and when the triamide is tricyclic, at least one of the chains between the nitrogens linked to phosphorus contains at least three atoms in the backbone.

DETAILED DESCRIPTION OF THE INVENTION

The compounds of this invention are bicyclic phosphorous triamides of the formula

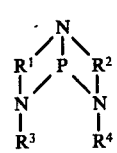

(1)

and, when $R^3$ and $R^4$ are joined together to form an alkylene group or interrupted alkylene group, the compounds are tricyclic phosphorous triamides of the formula

(2)

Examples of suitable $R^3$ and $R^4$ groups include alkyl such as methyl, propyl, t-butyl, and 1-ethyl-3-methylpentyl; cycloalkyl such as cyclopentyl and 2-methylcyclohexyl; and aralkyl such as benzyl, 1-naphthylmethyl, 1-methylphenethyl, and 7-phenylheptyl.

Suitable examples of $R^1$, $R^2$, and $R^8$ include ethylene, trimethylene, tetramethylene, pentamethylene, hexamethylene, 1,2-dimethylethylene, 2,2-dimethyltrimethylene, 1,3,3-trimethyltrimethylene. In compounds of formula (1) $R^1$ and $R^2$ are usually ethylene, —$CH_2CH_2$—, because of availability of the starting materials. When the compound is of formula (2), suitable examples of $R^8$ also include 3-azapentamethylene, 3-methyl-3-azapentamethylene, 3-octadecyl-3-azapentamethylene, 3-oxapentamethylene, and 3,6-dioxaoctamethylene.

Because it makes the products of formula (2) easier to form, at least one of $R^1$, $R^2$, and $R^8$ should contain at least three atoms in the backbone. When $R^8$ is of the formula

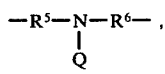

suitable examples of Q include
hydrogen, methyl, ethyl, isopropyl, t-butyl, isopentyl, 2-ethylhexyl, dodecyl and octadecyl. Preferably Q is hydrogen or a $C_1$ to $C_8$ alkyl group.

When $R^8$ is of the formula $-R^5-NH-R^6-$, the resulting product is a tautomeric mixture illustrated by the following structures:

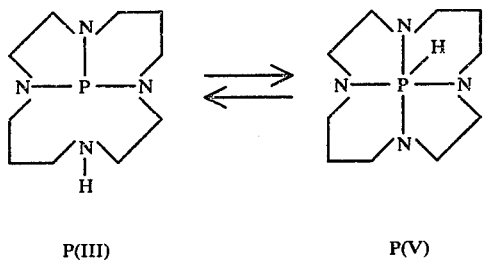

P(III)                    P(V)

These tautomeric forms are designated P(III) and P(V) based on the valence state of the phosphorus in the particular structure. Whether the product exists as principally P(III), principally P(V) or a mixture of these forms will depend on ring size and the location of the nitrogens in the starting cyclic polyamine. In some cases, the P(III) structure itself has tautomeric forms, for example

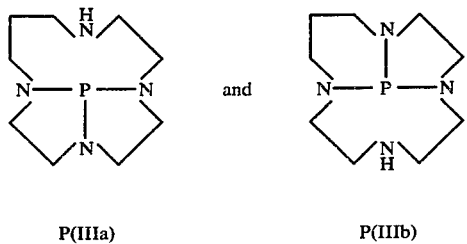

P(IIIa)                   P(IIIb)

In the claims, the products are designated by a P(III) structure. It is to be understood that this structure is intended to include the tautomeric isomers of the designated product.

The P(III)/P(V) tautomeric ratio can be determined by $^{31}$P-nmr. In this determination the chemical shifts, ppm from standard $H_3PO_4$, are assigned the same sign convention as in $^1$H-nmr. This characterization has a sensitivity of about 5%. In other words, an nmr spectra which indicates a pure tautomeric form does not preclude the presence of up to about 5% of another isomer.

The products of the invention are prepared by reacting the appropriate polyamine with a hexa(lower alkyl)-phosphorous triamide (also known as a tris[di(lower alkyl)amino]phosphine). The process can be represented by the following equation:

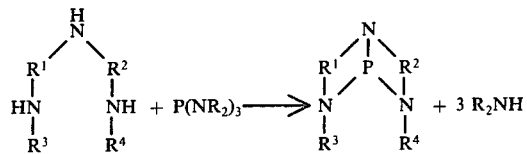

The chemical reaction involved is a transamidation, or amine exchange. The boiling point of the resulting di(-lower alkyl) amine, $R_2NH$, should be lower than that of either of the starting materials or of the polycyclic triamide product.

Suitable 1,7-dihydrocarbyldialkylenetriamines of the formula $R^3-NH-R^1-NH-R^2-NH-R^4$ for forming the bicyclic triamides of formula (1) are known, for example, 1,7-dimethyldiethylenetriamine, 1,7-bis(1-methylheptyl)diethylenetriamine, 1,7-dicyclopentyldiethylenetriamine, and 1,7-dibenzyldiethylenetriamine. These starting materials may be prepared by known alkylation methods such as reductive amination of an aldehyde or ketone. Reductive amination with an aldehyde is carried out in accordance with the equation:

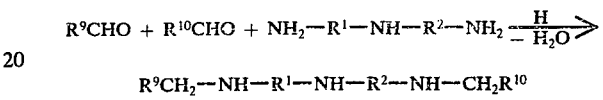

where $R^9CH_2-$ and $R^{10}CH_2-$ are $R^3$ and $R^4$ respectively.

Diethylenetriamine can be prepared by known methods. The higher dialkylenetriamines may be prepared by adaptations of these methods.

The cyclic polyamines used as starting materials for preparing the tricyclic triamides of formula (2) are prepared by the method outlined by Richman and Atkins in J. Amer. Chem. Soc., 96, 2268 (1974). Suitable examples of these cyclic polyamines include 1-oxa-4,7,10-triazacyclododecane, 1,4-dioxa-7,10,13-triazacyclopentadecane, 1,4,7,-triazacyclodecane, 1,5,9-triazacyclododecane, 1,8,15-triazacycloheneicosane, 1,4,8-triazacycloundecane, and 1,4,7,10-tetraazacyclododecane.

Hexamethylphosphorous triamide is the preferred triamide starting material, since it is commercially available and the resulting dimethylamine, bp 7° C, is easily eliminated from the reaction mixture.

The products of the invention are colorless, crystalline solids or colorless liquids that can be purified by sublimation and/or distillation. They are hydrolyzed by water and react slowly with atmospheric moisture and oxygen at room temperature. These products are useful as flame retardants for cellulosics such as cotton.

EXAMPLES OF THE INVENTION

The following examples illustrate the invention. All preparations were carried out in an atmosphere of nitrogen. Mass-spectral analyses were relied on to confirm the empirical formulas of the products. In each example, the product is designated by the predominant tautomeric structure.

EXAMPLE 1

10-Oxa-1,4,7-triaza-13-phosphatricyclo[5.5.1.0$^{4,13}$, ] tridecane is prepared as follows:

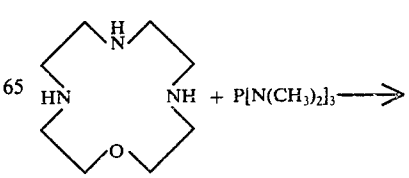

-continued

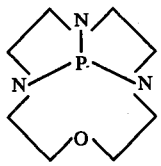 + 3 HN(CH$_3$)$_2$

A. A solution of 2.50 g of 1-oxa-4,7,10-triazacyclododecane and 2.35 g of hexamethylphosphorous triamide in 25 ml of toluene is refluxed for 40 hours. It is then concentrated to dryness in a rotary evaporator, to give 2.97 g (100%) of 10-oxa-1,4,7-triaza-13-phosphatricyclo[5.5.1.0$^{4,13}$]tridecane as a brittle, white solid. Sublimation at 80° C (0.007 mm) gives 2.08 g of white crystals having a melting point of 68°–70° C.

An infrared absorption spectrum of this material in mineral oil shows absorptions at 3.5, 6.82, 7.38, 7.59, 8.00, 8.24, 8.50, 8.83, 9.69, 9.89, 10.55, 11.18, 11.77, and 12.56μ.

B. 10-Oxa-1,4,7-triaza-13-phosphatricyclo[5.5.1.0$^{4,13}$]-tridecane is obtained in the absence of a solvent by heating 10.0 g of 1-oxa-4,7,10-triazatricyclododecane and 9.40 g of hexamethylphosphorous triamide at 75° C for 2 hours, by which time evolution of dimethylamine is complete. The product is sublimed at 80° C (0.40 mm) and identified by comparison of its infrared absorption spectrum with that of the product of part A. Mass-spectral analysis of this sample shows an M+ ion at 201; measured mass, 201.1094; calc'd, 201.1031; which confirms the empirical formula of the product of part A.

If 1,4-dioxa-7,10,13-triazacyclopentadecane were used in place of 1-oxa-4,7,10-triazacyclododecane in essentially the procedure of Example 1, the product would be

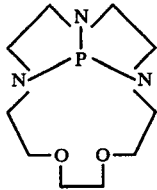

EXAMPLE 2

1,4,7-Triaza-11-phosphatricyclo[5.3.1.0$^{4,11}$] undecane is prepared as follows:

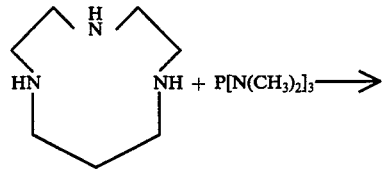

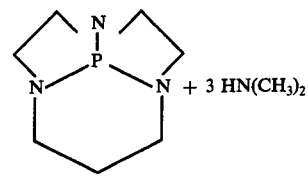

A. A solution of 5.00 g of 1,4,7-triazacyclodecane and 5.70 g of hexamethylphosphorous triamide in 50 ml. of toluene is refluxed for 48 hours. The toluene is removed under reduced pressure, and the residue is distilled through a short-path column, to give 5.31 g (89%) of 1,4,7-triaza-11-phosphatricyclo[5.3.1.0$^{4,11}$] undecane as a clear, colorless liquid having a boiling point of 96°–98° C at 0.70 mm. The product solidifies on standing at room temperature.

The infrared absorption spectrum (neat) of the product has absorptions at 3.5, 6.77, 7.01, 7.50, 7.78, 8.00, 8.24, 8.50, 8.78, 8.91, 9.12, 9.83, 10.10, 10.30, 10.8, 11.4, 12.4, and 12.8 μ.

B. 1,4,7-Triaza-11-phosphatricyclo[5.3.1.0$^{4,11}$]undecane is prepared in the absence of a solvent by heating the reactants of part A at 75° C for 1.5 hours, during which time dimethylamine is evolved. Distillation gives 5.48 g (92%) of the desired product which boils at 84°–86° C at 0.30 mm. The product is identified by comparison of its infrared absorption spectrum with that of the product of part A. Mass-spectral analysis shows an M+ ion at 171; measured mass, 171.0944; calc'd, 171.0925; which confirms the empirical formula of the product of part A.

EXAMPLE 3

1,5,9-Triaza-13-phosphatricyclo[7.3.1.0$^{5,13}$]tridecane is prepared as follows:

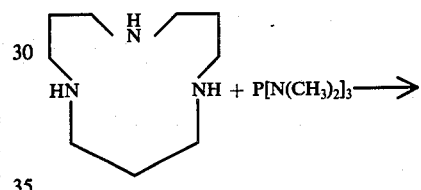

A mixture of 4.20 g of 1,5,9-triazacyclododecane and 4.00 g of hexamethylphosphorous triamide is heated at 100° C for about 6 hours, by which time evolution of dimethylamine is complete. Distillation under reduced pressure gives 3.70 g (76%) of 1,5,9-triaza- 13-phosphatricyclo[7.3.1.0$^{5,13}$]tridecane as a clear, colorless liquid which boils at 104°–135° C at 0.60 mm. The product solidifies at room temperature. Its infrared absorption spectrum (neat) shows absorptions at 3.5, 6.85, 7.01, 7.52, 7.73, 8.00, 8.27, 8.66, 8.90, 9.02, 9.36, 9.56, 10.27, 10.89, 11.42, 11.73, 11.97 and 14.7 μ. The mass spectrum shows an M+ ion at 199; measured mass, 199.1264; calc'd, 199.1238.

If 1,8,15-triazacycloheneicosane were used in place of 1,5,9-triazacyclododecane in essentially the procedure of Example 3, the product would be

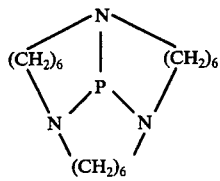

EXAMPLE 4

1,4,8-Triaza-12-phosphatricyclo[6.3.1.0^4,12]dodecane is prepared as follows:

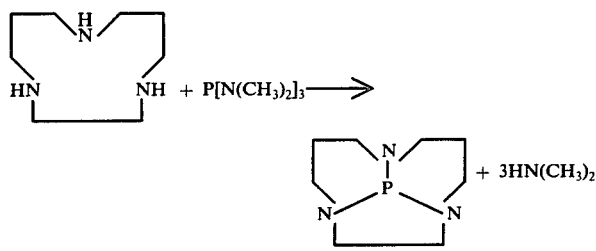

A mixture of 3.62 g of 1,4,8-triazacycloundecane and 3.75 g of hexamethylphosphorous triamide is heated to 125° C with stirring and held at this temperature for 2 hours, by which time evolution of dimethylamine is complete. Evolution is vigorous for the first 45 minutes. Distillation affords 3.20 g (75%) 1,4,8-triaza-12-phosphatricyclo[6.3.1.0^4,12]dodecane as a water-white liquid which boils at 73°–75° C at 0.30 mm.

The infrared absorption spectrum (neat) of the product has absorptions at 3.5, 7.46, 7.51, 8.00, 8.23, 8.70, 8.82, 8.96, 9.31, 9.78, 10.05, 10.5, 11.5, 11.7, and 14.4 μ. The mass spectrum shows an M+ ion at 181; measured mass, 181.1117; calc'd 181.1082.

EXAMPLE 5

2,8-Dimethyl-2,5,8-triaza-1-phosphabicyclo[3.3.0]octane is prepared as follows:

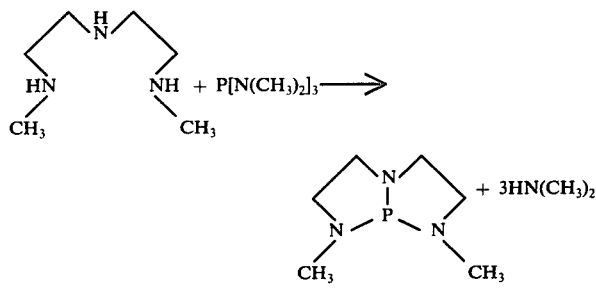

A mixture of 5.00 g of 1,7-dimethyldiethylenetriamine and 6.22 g of hexamethylphosphorous triamide is heated to 80° C, at which temperature dimethylamine begins to be evolved. Evolution of dimethylamine continues for about 1 hour, during which time the temperature is gradually raised to 125° C. The mixture is distilled to give 5.75 g (95%) of 2,8-dimethyl-2,5,8-triaza-1-phosphabicyclo[3.3.0]octane as a clear, colorless liquid, which boils at 55°–65° C at 0.30 mm. The nuclear magnetic-resonance spectrum (C₆D₆/TMS) of the product shows a highly split pattern from δ 2.0 to 4.5 and has the expected sharp doublet for the —CH₃ groups at δ2.55, J = 10 Hz. The infrared absorption spectrum (neat) has absorptions at 3.5, 6.83, 6.91, 7.65, 7.80, 8.20, 8.68, 9.20, 9.70, 10.15, 10.4, 10.7, and 11.5 μ.

On standing overnight at room temperature, the product turns into an immobile glass. This transformation can be inhibited by storage at a sufficiently low temperature.

If 1,7-dicyclopentyldiethylenetriamine were substituted for 1,7-dimethyldiethylenetriamine in essentially the procedure of Example 5, the product would be

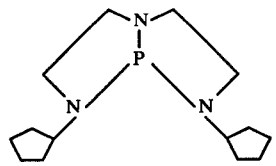

If 1,7-dibenzyldiethylenetriamine were substituted for 1,7-dimethyldiethylenetriamine in essentially the procedure of Example 5, the product would be 2,8-dibenzyl-2,5,8-triaza-1-phosphabicyclo[3.3.0]octane.

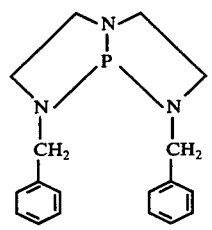

EXAMPLE 6

1,4,7,10-Tetraaza-13-phosphatetracyclo[5.5.1.0^4,13.0^10,13]triadecane is prepared as follows:

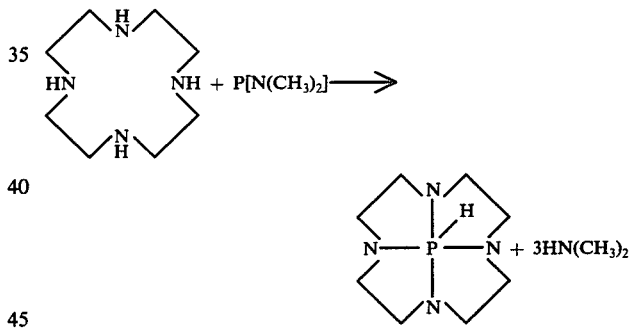

A. A solution of 1.75 g of 1,4,7,10-tetraazacyclododecane and 1.63 g of hexamethylphosphorous triamide in 50 ml of toluene is refluxed for 12 hours. Titration of the off-gases with 1 N HCl indicates that 97% of the theoretical amount of dimethylamine is evolved in this time. The toluene is removed under reduced pressure to give 2.0 g of 1,4,7,10-tetraaza-13-phosphatricyclo[5.5.1.0^4,13]tridecane as a white solid which melts at 109°–111° C with sintering from 90° C (possibly because of the presence of a trace of toluene). Sublimation of this product at 75° C and 0.55 mm gives large colorless crystals, which melt at 111°–113° C. The mass spectrum shows an M+ ion at 200; measured mass, 200.1194; calc'd, 200.1190.

B. 1,4,7,10Tetraaza-13-phosphatricyclo[5.5.1.0^4,13]tridecane is prepared in the absence of a solvent by heating 5.0 g of 1,4,7,10-tetraazacyclododecane and 4.7 g of hexamethylphosphorous triamide together at about 75° C for between two and three hours and subliming the crude product at 75° C at 0.4 mm. The yield is 5.3 g (92%) of product melting at 106°–108° C.

The nmr spectra of this material show absorptions at:

(minor). The relative integral of the two $^{31}$P absorbances indicates that the product has a P(III)/P(V) tautomeric ratio of 18/82.

A similarly prepared sample shows an M- ion in the mass spectrum at m/e 228.1524 (calcd m/e 228.1503, $C_{10}H_{21}N_4P$) and a strong M—H ion at m/e 227.1459 (calc'd m/e 227.1424, $C_{10}H_{20}N_4P$).

EXAMPLE 9

1,5,9,12-Tetraaza-15-phosphatricyclo 7.5.1.0$^{5,15}$]pentadecane is prepared as follows:

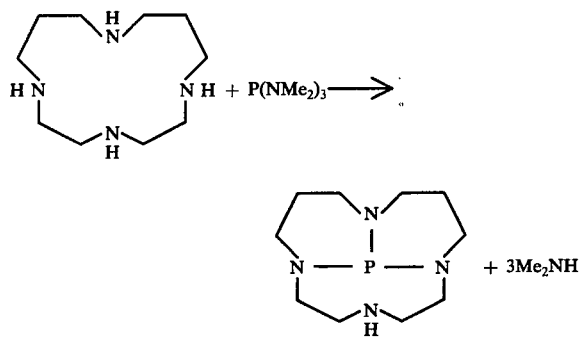

A stirred mixture of 6.00 g (30 mmol) of 1,4,7,11-tetraazacyclotetradecane and 4.90 g of hexamethylphosphorous triamide is heated under nitrogen for 3 hr at 120° and then distilled in a short-path apparatus to give 5.50 g (80%) of clear, colorless liquid 1,5,9,12-tetraaza-15-phosphatricyclo[7.5.1.0$^{5,15}$]pentadecane, bp 106°-110° (0.30 mm), which solidifies on storing below 0°.

The infrared spectrum of this material (neat) has absorptions at: 2.99 (w), 3.43, 4.60 (w, $\nu_{P-H}$), 6.82 6.96, 7.40, 7.60, 7.67, 7.93, 8.10, 8.47, 8.73, 8.83, 9.13, 9.62, 9.87, 10.00, 10.5, 11.7, 12.5, 14.0, 14.8 $\mu$.

The nmr spectrum of this material has absorptions at: ($^{31}$P, C$_6$D$_6$, ext H$_3$PO$_4$) $\delta$ 115.5, 112.9, 111.6, −53.0. The relative integral of the $^{31}$P absorbances indicates 88–90% P(III) structures.

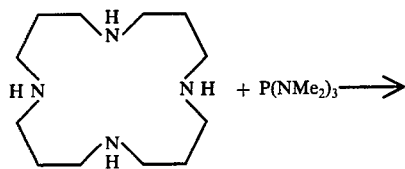

and 10–12% P(V) structure.

The mass spectrum of similarly prepared material has a parent ion at m/e 228.1508 (calc'd) m/e 228.1503) and other peaks at m/e 227 (M—H), 213, 200, 199, 172.

EXAMPLE 10

1,5,9,13-Tetraaza-17-phosphatricyclo[7.7.1.0$^{5,17}$]heptadecane is prepared as follows:

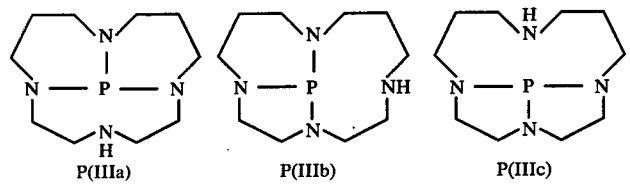

A mixture of 2.3 g of 1,5,9,13-tetaazacyclohexadecane and 1.8 g of hexamethylphosphorous triamide is heated under nitrogen at 125° for 2 hr and then distilled in a Kugelrohr apparatus to give 1.6 g of colorless liquid 1,5,9,13-tetraaza-17-phosphatricyclo[7.7.1.0$^{5,17}$]heptadecane, bp 110°-120° (0.1 mm), which solidifies on cooling to a white solid. The infrared spectrum of this material (CHCl$_3$ solution) has an absorption at 3.05 $\mu$ ($\nu_{N-H}$). N-H). The mass spectrum of this material shows ions at m/e 256, 255, 213, 157, 143, 84, 70, 58, 56 and 44.

A similar experiment with distillation of the product gives 76% yield of colorless liquid, bp 132°-135° (0.3 mm), which solidifies at room temperature.

The infrared spectrum (nujol) of this material has absorptions at 3.03, 7.45, 7.95, 8.55, 8.73, 8.95, 9.14, 9.43, 9.74, 10.98, 11.13, 11.28, 14.2 $\mu$.

The nmr spectra of this material have absorptions at: (60 MHz, $^1$H, C$_6$D$_6$TMS) $\delta$ 3.8-2.3 (16H, broad envelope), 2.0-1.0 (9H, broad envelope), ($^{31}$P, C$_6$D$_6$, ext H$_3$PO$_4$) $\delta$ 104.8, ($^{13}$C, C$_6$D$_6$/TMS) $\delta$ 49.7 (d, J = 37 Hz) 47.0 (d, J = 10 Hz), 46.7 (s), 44.9 (d, J = 7 Hz), 28.0 (d, J = 6 Hz) and 24.3 (s).

The products of the invention are useful as flame-retarding agents for cotton articles, as shown in the following examples.

EXAMPLE A

Two solutions are prepared, each containing the products of Example 1 or Example 6 in dimethylformamide (10 weight/volume %). Cotton swabs are soaked in these solutions, some for 10 minutes and some for 1 hour and all are dried overnight. Both the treated swabs and an untreated control are tested for flammability by holding them to a flame. The untreated control burns completely and glows after the flame extinguishes. All the treated swabs are self-extinguishing when removed from the flame; the swabs themselves are charred.

EXAMPLE B

Strips of cotton cloth are soaked overnight in 10 weight/volume % solutions of the products of Examples 1 and 6 in dimethylformamide and then dried. The treated fabrics, together with an untreated control, are tested for flammability by being held vertically and touched with a flame at their bottoms. The untreated control burns profusely. The fabric treated with the product of Example 1 self-extinguishes in less than 1 second and burns less than 5% of its length. The fabric treated with the product of Example 6 self-extinguishes in about 1 second and also burns about 5% of its length.

(60 MHz, ¹H, CDCl₃/TMS) δ 6.88 (1H, d, J = 628 Hz), 3.4–2.4 (16 H, m); (³¹P, C₆D₅, ext. H₃PO₄) δ −54.5 (d, J = 621 Hz); (¹³C, C₆D₆) δ 44.97 (d, J = 8.8 Hz).

The infrared absorption spectrum of the product in mineral oil has absorptions at 3.05 (very weak), 4.31, 7.51, 8.00, 8.20, 8.36, 8.92, 9.50, 10.22, 10.5, 11.5, 13.4 and 14.6 μ.

Measured mass (mass spec): 200.1226.

The infrared absorption of the product shows that it exists in tautomeric equilibrium with the structure

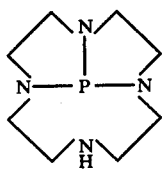

If 1-ethyl-1,4,7,10-tetraazacyclododecane were used in place of 1,4,7,10-tetraazacyclododecane in essentially the procedure of Example 6, the product would be of the formula

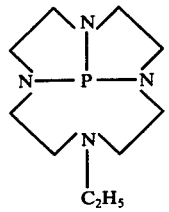

If 2,2,4,10,10,12-hexamethyl-1,5,9,13-tetraazacyclohexadecane were the starting material, the product would be of formula

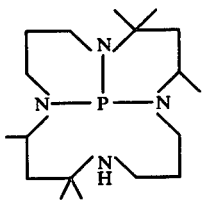

EXAMPLE 7

1,4,8,11-Tetraaza-14-phosphatetracyclo[6.5.1.0⁴,¹⁴.0¹¹,¹⁴]tetradecane is prepared as follows:

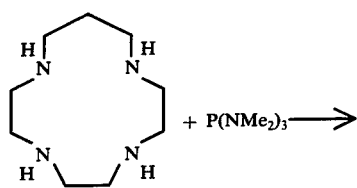

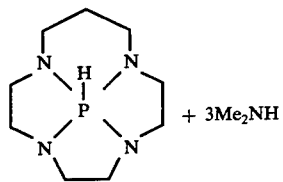

A mixture of 4.00 g (21.5 mmol) of 1,4,7,10-tetraazacyclotridecane and 3.50 g (21.5 mmol) of hexamethylphosphorous triamide is heated for 2 hr under nitrogen at 125° and then distilled under vacuum to give 3.84 g (83%) of clear, colorless, viscous liquid 1,4,8,11-tetraaza-14-phosphatetracyclo[6.5.1.0⁴,¹⁴.0¹¹,¹⁴]tetradecane, bp 92° (0.30 mm).

The infrared spectrum of this material (neat) has absorbances at 3.50, 4.43 (ν_{P-H}), 4.53, 6.84, 7.52, 7.8–8.8 (broad envelope), 9.10, 9.40, 9.64, 10.25, 11.1–11.5 (broad), 11.90, 13.95, and 14.9 μ.

The nmr spectra of this material have absorbances at: (60 MHz, ¹H, C₆D₆/TMS) δ 7.11 (1H, d, J = 609 Hz), 3.5–2.3 (16H, m), 1.42 (2H, octet); (³¹P, C₆D₆, ext H₃PO₄) δ − 61.1, J = 606 Hz; (¹³C, C₆D₆/TMS) δ 47.4 (d, J = 9.8 Hz), 47.1, 44.6 (d, J = 7.3 Hz), 44.0 (d, J = 7.3 Hz), and 25.0 (d, J = 1 Hz).

A similarly prepared sample shows a dominant M—H ion in the mass spectrum at m/e 213.1254 (calcd m/e 213.1268, C₉H₁₈N₄P).

EXAMPLE 8

1,4,8,11-Tetraaza-15-phosphatetracyclo 6.6.1.0⁴,¹⁵.0¹¹,¹⁵]pentadecane is prepared as follows:

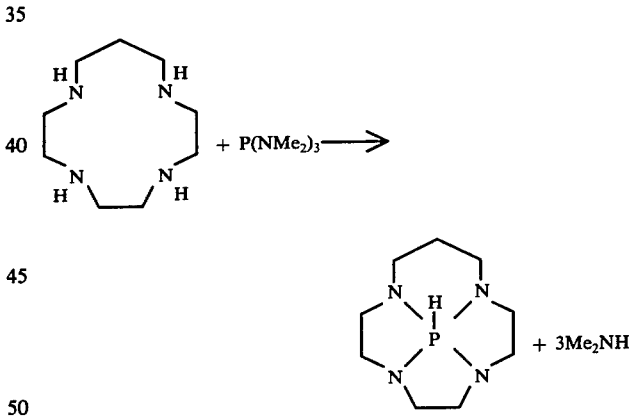

A stirred mixture of 4.90 g (30 mmol) of hexamethylphosphorous triamide, 6.00 g (30 mmol) of 1,4,8,11-tetraazacyclotetradecane, and 30 ml of dry toluene is heated to 80°–90°, under nitrogen for 16 hr, then refluxed for 8 hr. The hot solution is filtered under N₂ and concentrated, and the residue is sublimed at 60°–70° (0.3 mm) to give 5.45 g (80%) of waxy, white solid 1,4,8,11-tetraaza-15-phosphatetracyclo[6.6.1.0⁴,¹⁵.0¹¹,¹⁵]pentadecane.

The infrared spectrum of this material (nujol) has absorptions at 4.77 (ν_{P-H}), 7.51, 7.81, 8.02, 8.36, 8.63, 9.20, 9.47, 9.82, 10.29, 10.40, 11.05, 11.54, and 14.0 μ.

The nmr spectra of the material have absorbances at: (220 MHz, ¹H, C₆D₆/TMS) δ 5.84 (1H, d, J = 549 Hz), 3.20 (4H, broad mult.), 3.01 (4H, broad mult.), 2.52 (8H, sharp unsym. mult.), 1.60 (4H, sharp, unsym. mult.); (³¹P, C₆D₆, ext H₃PO₄) δ −53.1 (d, J_{PH} = 547 Hz), 111.9

What is claimed is:

1. Polycyclic phosphorous triamides of the formula

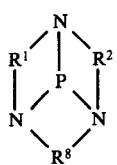

in which
R$^1$ and R$^2$, alike or different, are alkylene of 2 to 6 carbons containing at least 2 carbons in the backbone, and
R$^8$ is

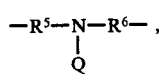

—R$^5$—O—R$^6$—, or
—R$^5$—O—R$^6$—O—R$^7$— where
R$^5$, R$^6$ and R$^7$, alike or different, are alkylene of 2 to 6 carbons containing 2 to 3 carbons in the backbone, and Q is hydrogen or alkyl of 1 to 18 carbons.

2. The tricyclic phosphorous triamides of claim 1 of the formula

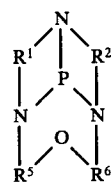

3. The tricyclic phosphorous triamides of claim 2 in which R$^1$, R$^2$, R$^5$ and R$^6$, alike or different, are alkylene of 2 to 3 carbons.

4. The tricyclic phosphorous triamide of claim 3 of the formula

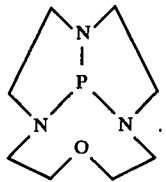

5. The tricyclic phosphorous triamides of claim 1 of the formula

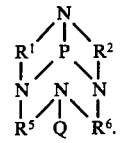

6. The tricyclic phosphorous triamide of claim 5 in which R$^1$, R$^2$, R$^5$ and R$^6$, alike or different, are alkylene of 2 to 3 carbons, and Q is H.

7. The tricyclic phosphorous triamide of claim 6 of the formula

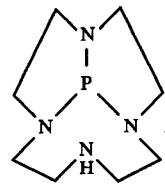

8. The tricyclic phosphorous triamide of claim 6 of the formula

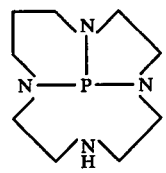

9. The tricyclic phosphorous triamide of claim 6 of the formula

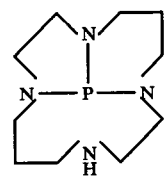

10. The tricyclic phosphorous triamide of claim 6 of the formula

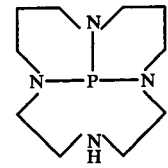

11. The tricyclic phosphorous triamide of claim 6 of the formula

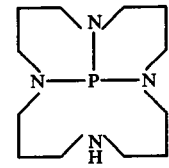

* * * * *

UNITED STATES PATENT OFFICE
CERTIFICATE OF CORRECTION

PATENT NO. : 4,038,312
DATED : July 26, 1977
INVENTOR(S) : Thomas Joseph Atkins

It is certified that error appears in the above-identified patent and that said Letters Patent are hereby corrected as shown below:

Column 10, line 40, the first formula should read as follows:

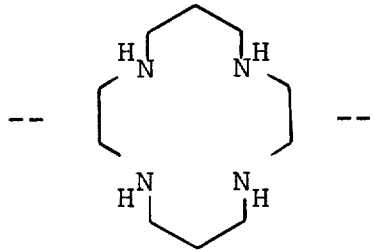

Column 10, line 47, the first formula should read as follows:

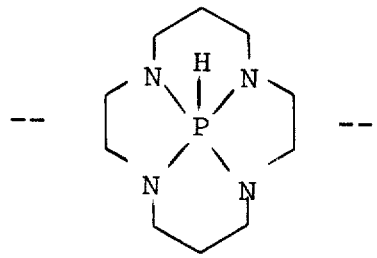

UNITED STATES PATENT OFFICE
CERTIFICATE OF CORRECTION

PATENT NO. : 4,038,312
DATED : July 26, 1977
INVENTOR(S) : Thomas Joseph Atkins

It is certified that error appears in the above-identified patent and that said Letters Patent are hereby corrected as shown below:

Column 11, line 4, "M-" should read -- $M^+$ --.

Column 11, line 10, "phosphatricyclo $7.5.1.0^{5,15}$]" should read -- phosphatricyclo $[7.5.1.0^{5,15}]$ --.

Signed and Sealed this

Twenty-first Day of March 1978

[SEAL]

Attest:

RUTH C. MASON
Attesting Officer

LUTRELLE F. PARKER
Acting Commissioner of Patents and Trademarks